(12) United States Patent
Meinke et al.

(10) Patent No.: US 6,221,894 B1
(45) Date of Patent: *Apr. 24, 2001

(54) NODULISPORIC ACID DERIVATIVES

(75) Inventors: Peter T. Meinke, New York, NY (US); Thomas L. Shih, Edison; Michael H. Fisher, Ringoes, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/269,010

(22) PCT Filed: Sep. 15, 1997

(86) PCT No.: PCT/US97/16242

§ 371 Date: Mar. 17, 1999

§ 102(e) Date: Mar. 17, 1999

(87) PCT Pub. No.: WO98/12196

PCT Pub. Date: Mar. 26, 1998

Related U.S. Application Data

(63) Continuation-in-part of application No. 08/716,012, filed on Sep. 19, 1996, now abandoned, which is a continuation-in-part of application No. 08/606,312, filed on Mar. 11, 1996, now abandoned, which is a continuation-in-part of application No. 08/406,619, filed on Mar. 20, 1995, now abandoned.

(51) Int. Cl.[7] ............. A61K 31/403; A61K 31/407; A61P 33/10; C07D 487/14

(52) U.S. Cl. ............................. 514/410; 548/417
(58) Field of Search ............... 514/410; 548/417

(56) References Cited

U.S. PATENT DOCUMENTS

| | | | |
|---|---|---|---|
| 5,015,630 | 5/1991 | Fisher et al. | 514/30 |
| 5,399,582 | 3/1995 | Dombrowski et al. | 514/410 |
| 5,595,991 | 1/1997 | Shoop et al. | 514/233.2 |
| 5,962,499 | * 10/1999 | Meinke et al. | 514/410 |

FOREIGN PATENT DOCUMENTS

| | | |
|---|---|---|
| 0 357460 | 3/1990 | (EP) . |
| 0 382173 | 8/1990 | (EP) . |
| 0 444964 | 9/1991 | (EP) . |
| 0 594291 | 4/1994 | (EP) . |
| 0 626375 | 11/1994 | (EP) . |
| WO 92/06582 | 4/1992 | (WO) . |
| WO 93/19053 | 9/1993 | (WO) . |
| WO 93/25543 | 12/1993 | (WO) . |
| WO 94/15944 | 7/1994 | (WO) . |
| WO 94/19334 | 9/1994 | (WO) . |
| WO 95/22552 | 8/1995 | (WO) . |
| WO 96/11945 | 4/1996 | (WO) . |
| WO 96/15121 | 5/1996 | (WO) . |

* cited by examiner

Primary Examiner—Jane C. Osswecki
(74) Attorney, Agent, or Firm—Shu M. Lee; David L. Rose

(57) ABSTRACT

The present invention relates to novel nodulosporic acid derivatives, which are acaricidal, antiparasitic, insecticidal and anthelmintic agents.

9 Claims, No Drawings

NODULISPORIC ACID DERIVATIVES

This is a 371 of PCT/US97/16242, filed Sep. 15, 1997 which is a continuation-in-part of U.S. Application Ser. No. 08/716,012, filed Sep. 19, 1996, now abandoned, which is a continuation-in-part of U.S. Application Ser. No. 08/606,312, filed Mar. 11, 1996, now abandoned, which is a continuation-in-part of U.S. Application Ser. No. 08/406,619, filed Mar. 20, 1995, now abandoned.

BACKGROUND OF THE INVENTION

Nodulosporic acid and two related components are antiparasitic agents and ectoparasiticidal agents isolated from the fermentation culture of Nodulisporium sp. MF-5954 (ATCC 74245). These three compounds have the following structures: nodulisporic acid (compound A)

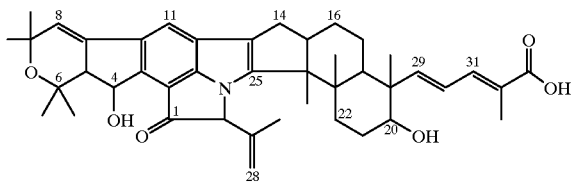

29,30-dihydro-20,30-oxa-nodulisporic acid (compound B)

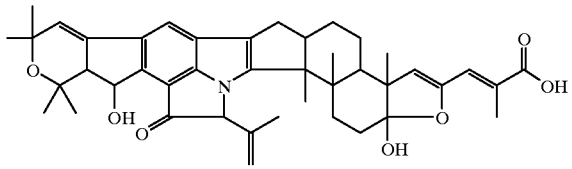

31-hydroxy-20,30-oxa-29,30,31,32-tetrahydro-nodulisporic acid (compound C)

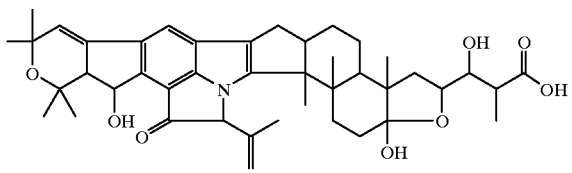

SUMMARY OF THE INVENTION

This invention relates to new acaricidal, antiparasitic, insecticidal and anthelmintic agents related to the nodulisporic acids, to processes for their preparation, compositions thereof, their use in the treatment of parasitic infections, including helminthiasis, in human and animals, and their use in the treatment of parasitic infections in plants or plant products.

DETAILED DESCRIPTION OF THE INVENTION

The present invention provides a compound having the formula I:

I

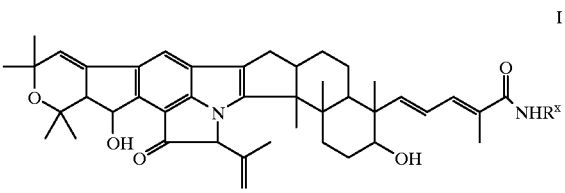

or a pharmaceutically acceptable salt thereof, wherein $R^x$ is selected from the group consisting of:

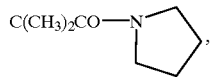

$CH_2CH_2CF_3$, $C(CH_3)_2CO_2CH_3$, $C(CH_3)_2CO_2CH_2CH_3$, $C(CH_3)_2CON(CH_3)_2$, $C(CH_3)_2CONHCH_2CF_3$, $C(CH_3)_2CON(CH_3)CH_2CH_3$, $CH(CH_2F)_2$, $C(CH_2F)_2CO_2CH_3$, $C(CH_3)_2CH_2F$, $C(CH_2F)_3$, and $C(CH_2F)_2CH_3$; or $R^x$ is a group derived from an amine selected from the group consisting of 1,1-dimethylpropylamine, 1,1-dimethylprop-2-enylamine, 3,4,4-trichlorobut-3-enylamine, 1,1,2-trimethylprop-2-enylamine, 1,1-dimethyl-2-trifluoromethylprop-2-enylamine, 3-methyoxypropylamine, 1,1-dimethylbutylamine, 4,4,4-trifluorobutylamine, 2,2,3,3,3-pentafluoropropylamine, 3,3,4,4,4-pentafluorobutylamine, 5,5,5-trifluoropentylamine, 1-fluoromethyl-2-fluoroethylamine, 1-methyl-2,2,2-trifluoroethylamine, 2-fluoromethyl-3-fluoropropylamine, 1,1-dimethyl-2,2,2-trifluoroethylamine, 2,2-difluoropropylamine, 3,3-difluorobutylamine, 2,2-difluorobutylamine, 2-methyl-3,3,3-trifluoropropylamine, 2,2,3,3,4,4,4-heptafluorobutylamine, 2,2-difluoro-3-methylbutylamine, 2-methyl-3,3,3-trifluoropropylamine, 3-methylbutylamine, 1,1-dimethyl-2-oxo4,4,4-trifluorobutylamine, 1,1-dimethyl-2-oxo-5,5,5-trifluoropentylamine, 1,1,3-trimethyl-2-oxobutylamine, 1,1,3,3-tetramethyl-2-oxobutylamine, propyl 2-amino-2-methylpropanoate, isopropyl 2-amino-2-methylpropanoate, phenyl 2-amino-2-methylpropanoate, 1,1-bis(fluoromethyl)-2-oxo-4,4,4-trifluorobutylamine, 1,1-bis(fluoromethyl)-2-oxo-3,3-dimethylbutylamine, 2-amino-2,2-bis(fluoromethyl)-(N-methyl-N-ethyl)acetamide, ethyl 2-amino- 2,2-bis(fluoromethyl)acetate, propyl 2-amino-2,2-bis(fluoromethyl)acetate, isopropyl 2-amino-2,2-bis(fluoromethyl)acetate, phenyl 2-amino-2,2-bis(fluoromethyl)acetate, 1,1-dimethyl-2-oxopropylamine, 1,1-dimethyl-2-oxobutylamine, 1,1,3-trimethyl-2-oxobutylamine, α,α-dimethyl-β-oxophenethylamine, 2,3-dimethyl-3-hydroxy-2-butylamine.

The present invention provides in another aspect pharmaceutical compositions comprising a compound of Formula I and a pharmaceutically acceptable carrier. Such compositions may further comprise one or more other active ingredients such as anthelmintic agents, insect regulators, ecdosyne agonists and fipronil.

The present invention provides in another aspect a method for treating parasitic diseases in a mammal which comprises administering an antiparasitic amount of a compound of Formula I. The treatment may further comprise co-administering one or more other active ingredients such as anthelmintic agents, insect regulators, ecdosyne agonists and fipronil.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds described herein contain one or more asymmetric centers and may thus give rise to diastereomers and optical isomers. The present invention is intended to include all possible diastereomers as well as their racemic and resolved, enantiomerically pure forms and all possible geometric isomers.

In addition, the present invention includes all pharmaceutically acceptable salts thereof. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable nontoxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Compounds of the present invention are named based on the trivial name of the parent compound, nodulisporic acid (compound A).

Compounds of the present invention are prepared from nodulisporic acid (Compound A) which in turn is obtained from the fermentation culture of Nodulisporium sp. MF-5954 (ATCC 74245). The description of the producing microorganism, the fermentation process, and the isolation and purification of the three nodulisporic acids are disclosed in U.S. Pat. No. 5,399,582, issued Mar. 21, 1995, which is hereby incorporated by reference in its entirety.

Compounds of formula I are prepared from the corresponding carboxylic acid using standard amide-forming reagents known to those skilled in the art. The reaction is carried out using at least one equivalent of an amine nucleophile, $H_2NR^x$, although preferably ten to one hundred equivalents of amine nucleophiles are employed. Amide-forming reagents include, but are not restricted to, dicyclohexylcarbodiimide, 1-(3diethylaminopropyl)-3-ethylcarbodiimide hydrochloride (EDC·HCl), diisopropylcarbodiimide, benzotriazol- 1-yloxy-tris (dimethylamino)phosphonium hexafluorphosphate (BOP), bis(2-oxo-3-oxazolidinyl)phosphinic chloride (BOP-Cl), benzotriazole-1-yl-oxy-tris-pyrrolidino-phosphonium hexafluorophosphate (PyBOP), chloro-tris-pyrrolidino-phosphonium hexafluorophosphate (PyCloP), bromo-tris-pyrrolidino-phosphonium hexafluorophosphate (PyBroP), diphenylphosphoryl azide (DPPA), 2-(1H-benzotriazole-1-yl)- 1,1,3,3-tetramethyluronium hexafluorophosphate (HBTU), O-benzotriazol-1-yl-N,N,N',N'-bis (pentamethylene)uronium hexafluorophosphate and 2-chloro-1-methylpyridinium iodide. The amide-forming reactions may be facilitated by the optional addition of N-hydroxybenzotriazole or N-hydroxy-7-aza-benzotriazole. The amidation reaction is generally performed using at least one equivalent (although several equivalents may be employed) of amine bases such as triethylamine, diisopropylethylamine, pyridine, N,N-dimethylaminopyridine and the like. The carboxyl group may be activated for amide bond formation via its corresponding acid chloride or mixed anhydride, using conditions known to those skilled in the art. These amide-forming reactions are carried out in aprotic solvents such as methylene chloride, tetrahydrofuran, diethyl ether, dimethylformamide, N-methylpyrrolidine and the like at −20° C. to 60° C. and are complete in 15 minutes to 24 hours.

The instant compounds are potent endo- and ecto-antiparasitic agents, particularly against helminths, ectoparasites, insects, and acarids, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have activity against these parasites, and in addition are also active against Dirofilaria in dogs and cats, Nematospiroides, Syphacia, Aspiculuris in rodents, arthropod ectoparasites of animals and birds such as ticks, mites such as scabies lice, fleas, blowflies, and other biting insects in domesticated animals and poultry, such as Tenophalides, Ixodes, Psoroptes, and Hemotobia, in sheep Lucilia sp., biting insects and such migrating dipterous larvae as Hypoderma sp. in cattle, Gastrophilus in horses, and Cuterebra sp. in rodents and nuisance flies including blood feeding flies and filth flies.

The instant compounds are also useful against parasites which infect humans. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acreage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

Accordingly, the present invention provides a method for the treatment or prevention of diseases caused by parasites which comprises administering to a host in need of such treatment or prevention an antiparasitic effective amount of a compound of Formula I. The parasites may be, for example, arthropod parasites such as ticks, lice, fleas, mites and other biting arthropods in domesticated animals and poultry. The parasites also include helminths such as those mentioned above.

Compounds of formula I are effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 500 mg per kg of animal body weight, such total dose being given at one time or in divided doses over a relatively short period of time such as 1–5 days. With the preferred compounds of the invention, excellent control of such parasites is obtained in animals by administering from about 0.025 to 100 mg per kg of body weight in a single dose. Repeat treatments are given as required to combat re-infections and are dependent upon the species of parasite and the husbandry techniques being employed. Repeat treatments may be given daily, weekly, biweekly, monthly, or longer for example up to six months, or any combination thereof, as required. The techniques for administering these materials to animals are known to those skilled in the veterinary field.

Compounds of formula I may be co-administered or used in combination with one or more other agents to the host. Co-administration or combination use includes administering all active ingredients in one formulation, for example a tablet, capsule, feed stuff, or liquid containing a compound of formula I and one or more said other agents; administering each ingredient in a separate formulation; and combinations thereof. When one or more of a compound of formula I or said other agent(s) is contained in a separate formulation, any order of administration as well as any interval between the administration of the active ingredients are within the meaning of co-administration or combination use.

Agents that may be co-administered or used in combination with compounds of formula I include any that are used in the treatment or prevention of human or animal diseases or conditions, or used in agricultural applications, or for pest control. In a preferred embodiment, the co-administered agents are used in veterinary medicine, particularly those used in domesticated animals such as dogs and cats or other companion animals. Examples of other agents that may be co-administered with compounds of formula I are provided below. It is to be understood that the specific agents enumerated are illustrative only, and are not meant to be restrictive in any manner.

Accordingly, compounds of the present invention may be co-administered or used in combination with anthelmintic agents. These anthelmintic agents are meant to include, but not be restricted to, compounds selected from the avermectin and milbemycin class of compounds such as ivermectin, avermectin, abamectin, emamectin, eprinamectin, doramectin, milbemycin derivatives described in EPO 357460, EPO 444964 and EPO 594291, moxidectin, Interceptor™ and nemadectin. Additional anthelmintic agents include the benzimidazoles such as thiabendazole, cambendazole, parbendazole, oxibendazole, mebendazole, flubendazole, fenbendazole, oxfendazole, albendazole, cyclobendazole, febantel, thiophanate and the like. Additional anthelmintic agents include imidazothiazoles and tetrahydropyrimidines such as tetramisole-levamisole, butamisole, pyrantel, pamoate, oxantel or morantel.

Compounds of this invention may be co-administered or used in combination with fipronil (FRONTLINE™); or with an insect growth regulator with molt inhibiting activity such as lufenuron (PROGRAM™) and the like; or with ecdysone agonists such as tebufenozide and the like, which induces premature molt and causes feeding to cease; or with imidacloprid (ADVANTAGE™).

Compounds of this invention may be co-administered or used in combination with avermectin or milbemycin or doramectin derivatives such as those described in U.S. Pat. No. 5,015,630, WO 94/15944, WO95/22552.

Compounds of this invention may be co-administered or used in combination with cyclic depsipeptides that exhibit anthelmintic efficacy such as those described in WO96/11945, WO93/19053, WO 93/25543, EP 626375, EP 382173, WO 94/19334, EP 382173 and EP 503538.

Compounds of this invention may be used in combination or be co-administered with derivatives and analogs of the general class of dioxomorpholine antiparasitic and anthelmintic agents as illustrated by WO 9615121; or with pyrethroids or organophosphates or insecticidal carbamates, such as those described in "Chemotherapy of Parasitic Diseases", Campbell, W. C. and Rew, R. S, Eds., 1986; or with derivatives and analogs of the general class of paraherquamide and macfortine anthelmintic agents.

The co-administered compounds are given via routes, and in doses, that are customarily used for those compounds.

Compounds of formula I may be administered orally in a unit dosage form such as a capsule, bolus or tablet including chewable tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 50% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 10% in the feed in order to achieve the desired anti-parasitic result.

In using the compounds of this invention, the individual compounds may be prepared and used in that form. Alternatively, mixtures of the individual compounds may be used, or they may be combined with other active compounds not related to the compounds of this invention.

Also included in the present invention are pharmaceutical compositions comprising a compound of formula I and a pharmaceutically acceptable carrier. The pharmaceutical compositions of the present invention may further comprise a second active ingredient such as those described above for co-administration. Preferred second ingredient is selected from an anthelmintic agent, fipronil, imidocloprid, an insect growth regulator, or a ecdysone agonist. Said second ingredient is preferably selected from the group consisting of: ivermectin, avermectin 5-oxime, abamectin, emamectin, eprinamectin, doramectin, doramectin monosaccharide 5-oximes, fulladectin, milbemycin, milbemycin 5-oxime, moxidectin, Interceptor™ (milbemycin oxime), nemadectin, imidacloprid, fipronil, lufenuron, thiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

The following examples are provided to more fully illustrate the present invention, and shall not be construed as limiting the scope in any manner.

EXAMPLE 1

General Procedure for the Preparation of Amide Derivatives of Nodulisporic Acid

To a solution of 30 mg of nodulisporic acid in 3 mL methylene chloride at 0° C. add 0.03 mL triethylamine and 12 mg N-hydroxybenzotriazole followed by 28 mg BOP reagent. Stir the solution for 10 minutes and then add 50 mg of amine selected from Table 1. Stir the solution overnight at 4° C. and then pour into 1/1 saturated sodium bicarbonate/brine, extract with methylene chloride and dry the combined organic layers over sodium sulfate. Remove the solids by filtration and concentrate the solution to dryness under reduced pressure. Pure product may be obtained by flash chromatography or preparative TLC on silica gel or reversed-phase liquid chromatography. The purified product may be characterized by proton NMR and mass spectrometry.

The general procedure was followed using the amines listed in Table 1 to produce the corresponding nodulisporamides. These compounds were characterized by proton NMR and/or mass spectrometry (m/z is for (M+1) unless otherwise specified).

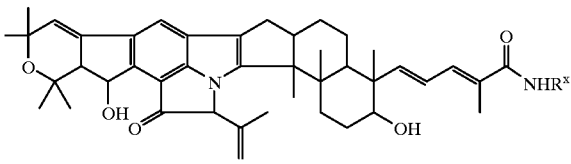

TABLE 1

Nodulisporamide Derivatives

| Ex. | m/z | Amines | $R^X$ |
|---|---|---|---|
| 1 | 774.9 | 3,3,3-trifluoropropylamine | $CH_2CH_2CF_3$ |
| 2 | 779.0 | methyl 2-amino-2-methyl-propanoate | $C(CH_3)_2CO_2CH_3$ |
| 3 | 793.1 | ethyl 2-amino-2-methyl-propanoate | $C(CH_3)_2CO_2CH_2CH_3$ |
| 4 | 792.1 | 2-amino-2-methyl-(N,N-dimethyl)propanamide | $C(CH_3)_2CON(CH_3)_2$ |
| 5 | 846.1 | 2-amino-2-methyl-(N-(2,2,2-trifluoroethyl))propanamide | $C(CH_3)_2CONHCH_2CF_3$ |
| 6 | 806.1 | 2-amino-2-methyl-(N-ethyl-N-methyl)propanamide | $C(CH_3)_2CON(CH_3)CH_2CH_3$ |
| 7 | 756.9 | 1,3-difluoro-2-propylamine | $CH(CH_2F)_2$ |
| 8 | 818.1 | N-(2-amino-2-methyl-propanoyl)pyrrolidine | 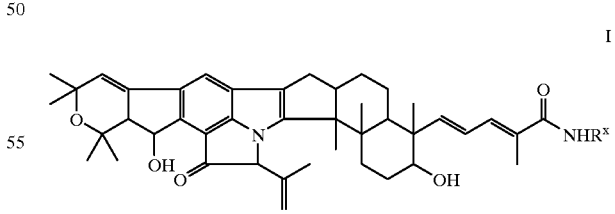 |
| 9 | 815.0 | methyl 2-amino-2,2-bis(fluoromethyl)acetate | $C(CH_2F)_2CO_2CH_3$ |

TABLE 1-continued

Nodulisporamide Derivatives

| Ex. | m/z | Amines | $R^X$ |
|---|---|---|---|
| 10 | 753.5 | 1,1-dimethyl-2-fluoroethylamine | $C(CH_3)_2CH_2F$ |
| 11 | 771.8 | 1,1-bis(fluoromethyl)ethylamine | $C(CH_2F)_2CH_3$ |
| 12 | 789.4 | 1,1-bis(fluoromethyl)-2-fluoroethylamine | $C(CH_2F)_3$ |

Following the general procedure and using the amines listed in Table 2, the corresponding nodulisporamide derivatives are prepared.

Table 2: Amines for the Preparation of Additional Nodulisporamide Derivatives 1,1-dimethylpropylamine, 1,1-dimethylprop-2-enylamine, 3,4,4-trichlorobut-3-enylamine, 1,1,2-trimethylprop-2-enylamine, 1,1-dimethyl-2-trifluoromethylprop-2-enylamine, 3-methyoxypropylamine, 1,1-dimethylbutylamine, 4,4,4-trifluorobutylamine, 2,2,3,3,3-pentafluoropropylamine, 3,3,4,4,4-pentafluorobutylamine, 5,5,5-trifluoropentylamine, 1-fluoromethyl-2-fluoroethylamine, 1-methyl-2,2,2-trifluoroethylamine, 2-fluoromethyl-3-fluoropropylamine, 1,1-dimethyl-2,2,2-trifluoroethylamine, 2,2-difluoropropylamine, 3,3-difluorobutylamine, 2,2-difluorobutylamine, 2-methyl-3,3,3-trifluoropropylamine, 2,2,3,3,4,4,4-heptafluorobutylamine, 2,2-difluoro-3-methylbutylamine, 2-methyl-3,3,3-trifluoropropylamine, 3-methylbutylamine, 1,1-dimethyl-2-oxo4,4,4-trifluorobutylamine, 1,1-dimethyl-2-oxo-5,5,5-trifluoropentylamine, 1,1,3-trimethyl-2-oxobutylamine, 1,1,3,3-tetramethyl-2-oxobutylamine, propyl 2-amino-2-methylpropanoate, isopropyl 2-amino-2-methylpropanoate, phenyl 2-amino-2-methylpropanoate, 1,1-bis(fluoromethyl)-2-oxo-4,4,4-trifluorobutylamine, 1,1-bis(fluoromethyl)-2-oxo-3,3-dimethylbutylamine, 2-amino-2,2-bis(fluoromethyl)-(N-methyl-N-ethyl)acetamide, ethyl 2-amino-2,2-bis(fluoromethyl)acetate, propyl 2-amino-2,2-bis(fluoromethyl)acetate, isopropyl 2-amino-2,2-bis(fluoromethyl)acetate, phenyl 2-amino-2,2-bis(fluoromethyl)acetate, 1,1-dimethyl-2-oxopropylamine, 1,1-dimethyl-2-oxobutylamine, 1,1,3-trimethyl-2-oxobutylamine, α,α-dimethyl-β-oxophenethylamine, 2,3-dimethyl-3-hydroxy-2-butylamine.

What is claimed is:
1. A compound having the formula I:

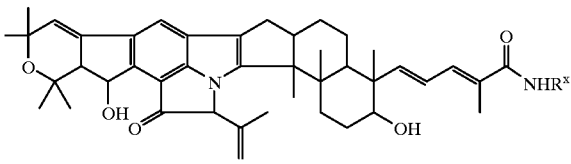

I or a pharmaceutically acceptable salt thereof, wherein $R^X$ is selected from the group consisting of: $C(CH_2F)_3$, and $C(CH_2F)_2CH_3$; or $R^X$ is a 1,1-dimethylpropyl, 1,1-dimethylprop-2-enyl, 3,4,4-trichlorobut-3-enyl, 1,1,2-trimethylprop-2-enyl, 1,1-dimethyl-2-trifluoromethylprop-2-enyl, 3-methyoxypropyl, 1,1-dimethylbutyl, 4,4,4-trifluorobutyl, 2,2,3,3,3-pentafluoropropyl, 3,3,4,4,4-pentafluorobutyl, 5,5,5- trifluoropentyl, 1-fluoromethyl-2-fluoroethyl, 1-methyl-2,2,2-trifluoroethyl, 2-fluoromethyl-3-fluoropropyl, 1,1-dimethyl-2,2,2-trifluoroethyl, 2,2-difluoropropyl, 3,3,3-difluorobutyl, 2,2-difluorobutyl, 2-methyl-3,3,3-trifluoropropyl, 2,2,3,3,4,4,4-heptofluorobutyl, 2,2-difluoro-3-methylbutyl, 2-methyl-3,3,3-trifluoropropyl, 3-methylbutyl, 1,1-dimethyl-2-oxo-4,4,4-trifluorobutyl, 1,1-dimethyl-2-oxo-5,5,5-trifluoropentyl, 3,1,1,3-trimethyl-2-oxobutyl, 1,1,3,3-tetramethyl-2-oxobutyl, (propyl 2-methylpropanoate)-2yl, (isopropyl 2-methylpropanoate)-2-yl, (phenyl 2-methylpropanoate)-2-yl, 1,1-bis(fluoromethyl)-2-oxo-4,4,4-trifluorobutyl, 1,1-bis(fluoromethyl)-2-oxo-3,3-dimethylbutyl, 2,2-bis(fluoromethyl)-(N-methyl-N-ethyl)acetamide)-2-yl, ethyl 2,2-bis(fluoromethyl)acetate)-2yl, propyl 2,2-bis(fluoromethyl)acetate)-2-yl, isopropyl 2,2-bis(fluoromethyl)acetate, phenyl 2,2-bis(fluoromethyl)acetate)-2-yl, 1,1-dimethyl-2-oxopropyl, 1,1-dimethyl-2-oxobutyl, 1,1,3-trimethyl-2-oxobutyl, α,α-dimethyl-β-oxophenethyl, or 2,3-dimethyl-3-hydroxy-2-butyl group.

2. A compound of claim 1 wherein $R^x$ is selected from the group consisting of:

$C(CH_2F)_3$, and $C(CH_2F)_2CH_3$.

3. A pharmaceutical composition comprising a compound of claim 1 and a pharmaceutically acceptable carrier.

4. A composition of claim 3 further comprising an anthelmintic agent.

5. A composition of claim 4 wherein said anthelmintic agent is selected from the group consisting of: ivermectin, avermectin 5-oxime, abamectin, emamectin, eprinamectin, doramectin, doramectin monosaccharide 5-oximes, fulladectin, milbemycin, milbamycin 5-oxime, moxidectin, Interceptor™, nemadectin, imidacloprid, fipronil, lufenuron, thiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

6. A composition of claim 3 further comprising fipronil, imidacloprid, lufenuron or an ecdysone agonist.

7. A method for the treatment or prevention of a parasitic disease in a mammal which comprises administering to said mammal an antiparasitic effective amount of a compound of claim 1.

8. A method of claim 7 further comprising co-administering to said mammal a therapeutically effective amount of an anthelmintic agent.

9. A method of claim 7 further comprising co-administering to said mammal a therapeutically effective amount of fipronil, imidacloprid or lufenuron.

* * * * *